United States Patent [19]

Sowerby

[11] 4,081,386
[45] Mar. 28, 1978

[54] REACTION MIXTURES FROM REACTING DI- AND TRIAZINES WITH SULFUR-CONTAINING COMPOUNDS AND LUBRICANTS AND FUELS CONTAINING THE SAME

[75] Inventor: Roger L. Sowerby, Mentor, Ohio

[73] Assignee: The Lubrizol Corporation, Wickliffe, Ohio

[21] Appl. No.: 728,586

[22] Filed: Oct. 1, 1976

[51] Int. Cl.$^2$ .................. C10M 1/48; C10M 3/42; C10M 5/24; C10M 7/46
[52] U.S. Cl. .................. 252/32.7 E; 44/63; 252/32.5; 252/47; 252/47.5; 252/46.7; 252/51.5 A; 252/400 A; 252/402; 252/403
[58] Field of Search .............. 44/63; 252/46.7, 47.5, 252/32.5, 32.7 E, 47, 51.5 A, 400 A, 402, 403

[56] References Cited

U.S. PATENT DOCUMENTS

| | | | |
|---|---|---|---|
| 2,304,624 | 12/1942 | Burke | 260/248 NS |
| 2,321,989 | 6/1943 | Burke | 260/248 NS |
| 2,706,194 | 4/1955 | Morris et al. | 252/46.7 |
| 3,377,275 | 4/1968 | Michalski et al. | 252/47.5 |
| 3,763,094 | 10/1973 | Knell et al. | 252/47.5 |

Primary Examiner—Delbert E. Gantz
Assistant Examiner—Irving Vaughn
Attorney, Agent, or Firm—James W. Adams, Jr.; Daniel N. Hall

[57] ABSTRACT

Reaction mixtures made from reacting one or more substituted di- and triazines of the formula:

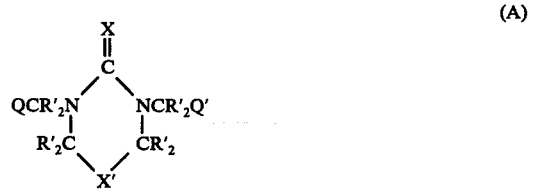

(A)

wherein Q and Q' are each independently halo, hydrocarbyloxy of the formula —OR and hydrocarbyl of the formula —R, wherein each R independently contains up to about 20 carbon atoms, with the proviso that at least one of Q and Q' is either hydrocarbyloxy or halogen; X and X' are each independently oxygen, divalent sulfur, =NH, and =NR$_1$ wherein R$_1$ is hydrocarbyl up to about 20 carbon atoms; and each R' is independently hydrogen or hydrocarbyl of up to about 10 carbon atoms; with (B) one or more mercapto compounds such as mercaptans, thiolphosphorus acids, thiocarbamates, and thiocarbonates are useful in fuels and lubricants.

58 Claims, No Drawings

REACTION MIXTURES FROM REACTING DI- AND TRIAZINES WITH SULFUR-CONTAINING COMPOUNDS AND LUBRICANTS AND FUELS CONTAINING THE SAME

This invention relates to nitrogen and sulfur containing compositions made by the reaction of substituted di- and triazine compounds with mercapto compounds. It also relates to lubricants and normally liquid fuels containing such compositions, as well as concentrates for forming the lubricant and fuel compositions.

Synthesis of substituted di- and triazine compounds by α-ureidoalkylation has been reviewed by H. Peterson in SYNTHESIS, INTERNATIONAL JOURNAL OF METHODS IN SYNTHETIC ORGANIC CHEMISTRY, No. 5, May 1973, pages 243–292. This article describes the preparation of 4-oxotetrahydro-1,3,5-oxadiazines by reaction of disubstituted urea in 1:2 molar ratio with formaldehyde in the presence of acid.

It also reports that according to some earlier work, the reaction of ureas with formaldehyde and an alcohol may give 3-alkoxymethyl-5-alkyl or 3,5-dialkoxymethyl derivatives of 4-oxotetrahydro-1,3,5-oxadiazines. Further, it is reported according to this earlier work that these mono- and di-alkoxy compounds can react with mercaptans in the presence of acids to form either 3-alkylmercaptomethyl-5-alkyl or 3,5-dialkylmercaptomethyl-4-oxotetrahydro-1,3,5-oxadiazines corresponding, respectively, to the following formulae:

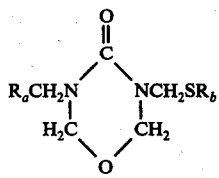

(i)

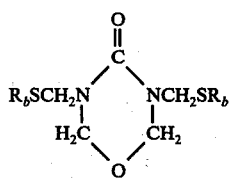

(ii)

wherein $R_a$ is shown to be hydrogen or methyl and $R_b$ is shown to be ethyl.

Also described in the Peterson article is the reaction of 3-alkoxymethyl-4-oxotetrahydro-1,3,5-oxadiazines with thionyl halides to form 3-halomethyl-4-oxotetrahydro-1,3,5-oxadiazines which can, according to the Peterson article, supra, be reacted with trialkyl phosphites to form dialkyl-4-oxotetrahydro-1,3,5-oxadiazin-3-ylmethanephosphonates of the formula:

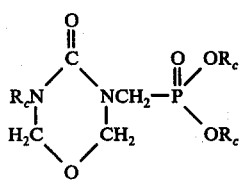

wherein $R_c$ is methyl.

It is a primary object of this invention to provide novel compositions of matter suitable for use in fuel and lubricant compositions. It is a further object of this invention to provide processes for making these compositions. It is a still further object of this invention to provide novel fuel and lubricant compositions as well as to provide novel concentrates for forming these fuel and lubricant compositions. The manner for accomplishing these and other objects will be apparent to those of ordinary skill in the art from the following detailed description of the invention.

This invention comprises compositions of matter which are reaction mixtures made by reacting (A) at least one of the substituted di- or triazine compounds of the formula:

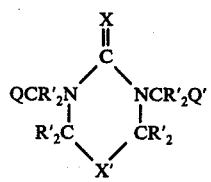

wherein Q and Q' are each independently selected from the group consisting of halo, hydrocarbyloxy of the formula —OR, and hydrocarbyl of the formula —R, wherein each R independently contains up to about 20 carbon atoms, with the proviso that at least one of Q and Q' is hydrocarbyloxy or halo; X and X' are independently selected from the group consisting of oxygen, divalent sulfur, =NH, and =NR$_1$, wherein R$_1$ is as R above; and each R' is independently hydrogen or hydrocarbyl of up to 10 carbon atoms; with (B) at least one mercapto compound or salt thereof of the formula:

ZSY wherein Y is selected from the group consisting of hydrogen, a Group I or an equivalent of a Group II metal cation or an ammonium cation containing up to about 20 carbon atoms or mixtures of two or more of these, and Z is selected from the group consisting of:

(1) hydrocarbyl groups of the formula —R" having from 4 to about 40 carbon atoms
(2) phosphorus acid groups of the formula

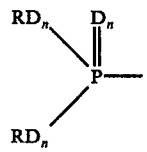

wherein each R is defined as in (A); each $n$ is independently zero or 1; and each D is independently oxygen or divalent sulfur;

(3) amido-carbo groups of the formula

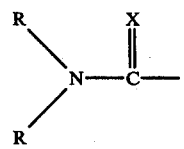

wherein each R and X are defined as in (A);

(4) hydrocarbyloxycarbo groups and sulfur-containing analogs of the formula

wherein R and D are defined as in (B) (2) above; and (5) mixtures of any two or more of any of the groups within (B) (1), (B) (2), (B) (3), and/or (B) (4), provided that when neither of Q and Q' is hydrocarbyloxy, then Y is a Group I or an equivalent of a Group II metal cation.

This invention also includes lubricating compositions, normally liquid fuels, and additive concentrates containing the reaction mixtures of (A) and (B). It also includes sulfurized products of (A) with (B) and fuels, lubricants and additive concentrates containing such sulfurized products.

As used herein ("herein" includes the appended claims), the terminology "hydrocarbyl" or "hydrocarbyl group" refers to monovalent carbon and hydrogen-containing groups such as aliphatic, cycloaliphatic, aromatic, mixed-aliphatic-cycloaliphatic, mixed-aliphatic-aromatic, and mixed-cycloaliphatic-aromatic.

As used herein, the terminology "hydrocarbyl" and "hydrocarbyl group" is inclusive of substantially equivalent groups formed by replacing hydrogen from a purely hydrocarbyl or hydrocarbyl group (i.e., purely meaning that it contains only carbon and hydrogen) with certain non-reactive, or substantially non-reactive (in the context of this invention) substituents containing atoms which are neither hydrogen nor carbon. The important factor, with respect to these substituted hydrocarbyl or substantially hydrocarbyl groups, is that the presence of atoms which are neither hydrogen nor carbon should not significantly alter the characteristics and properties of a compound or group relative to either an analogous purely hydrocarbyl group or a compound containing the purely hydrocarbyl group.

The type and degree of substitution of the "hydrocarbyl" and "hydrocarbyl group" will be understood by those or ordinary skill in the art to which this invention pertains. For example, chemically impure reactants (i.e., those containing minor amounts of hydrocarbyl groups substituted with non-reactive or substantially non-reactive substituents) are, for economic reasons, often used rather than the corresponding "purely hydrocarbyl" reactant. Similarly, methoxy-substituted or nitro-substituted dodecenyl is the substantial equivalent of dodecenyl for purposes of this invention. Representative substituents which may replace hydrogen are halo (e.g., chloro, bromo, iodo); alkoxy (especially lower alkoxy); alkylthio (especially lower alkylthio such as ethylthio, propylthio, pentylthio, etc.); mercapto; cyano; nitro; keto; carbamyl; hydroxy; carbo-lower alkoxy such as carboethoxy; and the like, as well as hetero or interrupting atoms such as sulfur, oxygen (e.g., polyoxyalkylene), and nitrogen.

Normally, when the reaction mixtures of the invention are to be used as lubricant and fuel additives, the degree of substitution and nature of substituents is such that the essential hydrocarbon character of the "hydrocarbyl" or "hydrocarbyl group" is not altered in a significant way. In view of this requirement, there may normally be up to about one such substituent for each 6 carbon atoms; more often no more than about one such substituent for each 12 carbon atoms. Normally, "hydrocarbyl" and "hydrocarbyl groups" of purely hydrocarbyl character are used; that is, those free from atoms other than carbon and hydrogen.

The hydrocarbyl and hydrocarbyl groups are substantially saturated. The terminology "substantially saturated" is intended to define groups which are free from acetylenic unsaturation (—C≡C—) and in which there is not more than one, if any, ethylenic linkage (—C=C—) for every eight carbon-to-carbon covalent bonds. The so-called double bonds in an aromatic ring (e.g., benzene), are not considered as contributing to unsaturation with respect to the terminology "substantially saturated". Usually there will be no more than an average of one ethylenic linkage per substantially saturated group. Preferably, all the carbon-to-carbon bonds in a substantially saturated group will be saturated linkages; i.e., the group will be free from acetylenic or ethylenic unsaturation.

The following are representative examples of hydrocarbyl groups: (1) alkyl, such as ethyl, t-butyl, isooctyl, dodecyl and eicosyl; (2) cycloalkyl, such as cyclooctyl and cyclobutyl; (3) aryl, such as phenyl, naphthyl, and diphenyl; (4) cycloalkylalkyl, such as cyclopropylethyl and cyclooctylbutyl; (5) arylalkyl, such as benzyl, phenylethyl, tolyldecyl and naphthylethyl; (6) alkylcycloalkyl, such as trimethylcyclododecyl and butylcycloheptyl; (7) arylcycloalkyl, such as xylylcyclodecyl and naphthylcyclohexyl; (8) alkylaryl, such as tolyl, xylyl, dodecylphenyl and didodecylphenyl; and (9) cycloalkylaryl, such as cyclobutylphenyl and cyclohexylnaphthyl. When a named group has several isomeric forms, all such forms are included.

Typical of such hydrocarbyl groups are those selected from the group consisting of alkyl, phenyl, naphthyl, alkylphenyl, alkylnaphthyl, phenylalkyl, naphthylalkyl and alkylnaphthylalkyl. Alkyl, alkaryl or aryl groups are normally the more preferred hydrocarbyl groups, particularly alkyl. Of course, these preferred hydrocarbyl groups may also contain minor amounts of the non-reactive or substantially non-reactive substituents as set out above.

The terminology "hydrocarbyloxy" or "hydrocarbyloxy group" as used herein refers to hydrogen and carbon containing groups as described above, but, in contrast to these "hydrocarbyl" or "hydrocarbyl groups", have a terminal oxy (—O—) group connecting them to the remainder of the compound of which they are a part. These "hydrocarbyloxy" or "hydrocarbyloxy groups" may contain certain non-reactive or substantially non-reactive substituents as previously described and exemplified with respect to "hydrocarbyl" and "hydrocarbyl group". Exemplary hydrocarbyloxy or hydrocarbyloxy groups include alkoxy such as methoxy, butoxy, hexyloxy, isooctyloxy, and 9-ethylhexadecyloxy, alkaryloxy such as dodecylphenoxy and trifluoromethylphenoxy, arylalkoxy such as tolyldecyloxy and phenylethoxy; aryloxy such as p-nitrophenoxy and naphthoxy, cycloalkyloxy such as cyclopentyloxy and cyclohexyloxy, alkoxyaryloxy such as ethoxyphenyloxy and butoxynaphthoxy.

The terminology "lower alkyl", "lower alkoxy", "halogen" and "halo" as used herein has the following definitions. Lower alkyl refers to a straight or branched chain alkyl group containing up to 7 carbon atoms. Accordingly, this terminology includes alkyl groups such as methyl, ethyl, tertiary butyl, isoamyl and heptyl. Similarly, "lower alkoxy" refers to analogous lower alkyl groups with terminal oxy (—O—) groups; for example, ethoxy, isoamyloxy, etc.). Halo or halogen includes fluoro, chloro, bromo and iodo. The preferred halo groups are normally chloro and bromo.

This invention is not dependent upon any particular route for the preparation of the substituted di- and triazine compounds (A) and any conventional process can be employed for the preparation of these compounds. Preferred di- and triazine compounds (A) are those wherein at least one, preferably both, of Q and Q' are hydrocarbyloxy. These preferred compounds can be prepared as hereinafter disclosed.

One route for the preparation of substituted tetrahydrooxadiazine compounds of (A) which are of the formulae:

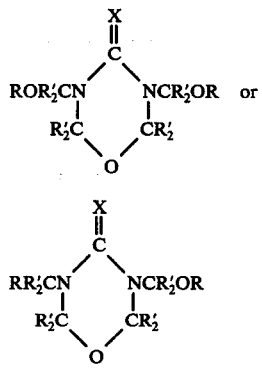

I

II (that is, wherein Q and Q' are hydrocarbyloxy and/or hydrocarbyl) wherein R, R' and X are as stated hereinbefore, involves the reaction of a ureido component (e.g., urea, thiourea, guanidine, N-methylurea, N-propyl thiourea, etc.) with an aldehyde or ketone of the formula

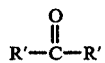

and an alcohol of the formula ROH. The terminology "ureido component", as used herein refers to one or more aliphatic compounds having the functional grouping

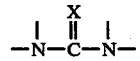

wherein X is hereinbefore defined and each nitrogen has at least one replacable hydrogen with the other valence being independently satisfied by, for example, hydrogen, monovalent hydrocarbyl (e.g., lower alkyl, phenyl), or other such groups. Thus, for example, urea or N-substituted urea (e.g., N-lower alkylurea), formaldehyde and methanol can be reacted, under known conditions, to form substituted oxotetrahydrooxadizine compounds of the formulae:

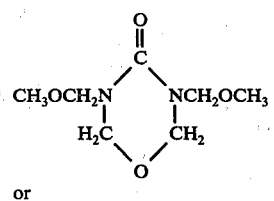

IA or

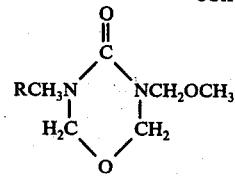

IIA wherein R is previously defined.

The process conditions for the preparation of compounds of formulae IA and IIA can be in accordance with those in the first above-cited Peterson article, which is in the interest of brevity, incorporated herein by reference, particularly pages 243 to 253. Similarly, other ureido components, aldehydes or ketones, (e.g., $C_2$-$C_7$ aldehydes and ketones) and alcohols (e.g., $C_2$-$C_7$ alcohols) can be reacted to provide other desired compounds within formulae I and II above, and these other compounds, of course, are contemplated herein.

In formulae I and II above, X is preferably oxygen, R is preferably alkyl, particularly lower alkyl; and R' is preferably lower alkyl, particularly hydrogen.

Substituted triazine compounds within (A) also include those of the formulae:

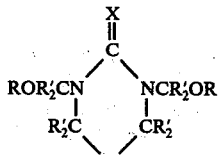

III

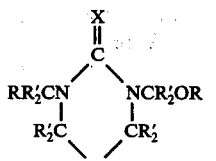

IV

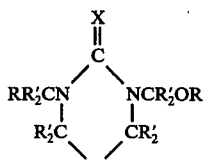

V

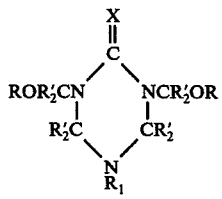

VI wherein R, R', $R_1$ and X are above-described. These compounds of III to VI can be prepared according to known processes as, for example, is disclosed in U.S. Pat. No. 2,321,989, which is herein incorporated by reference. One process disclosed in U.S. Pat. No. 2,321,989 is the reaction of urea and formaldehyde in such proportions that a tetramethylolurea is formed which is then reacted with a primary amine (e.g., alkylamine) to give the dimethylol derivative of a tetrahydrotriazine, which on subsequent treatment with an alcohol of the formula ROH, gives compounds of formulae IV and VI.

A route in the preparation of substituted triazine compounds of formulae III and V also involves known reactions such as is disclosed in U.S. Pat. No. 2,304,624 (which is hereby herein incorporated by reference for its relevant disclosure) with an aldehyde (particularly formaldehyde) and an alcohol (particularly a lower alkanol). The procedure of U.S. Pat. No. 2,304,624 produces precursors to the compounds of formulae III and V. These precursors, which are of the formulae:

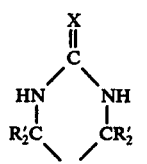           IIIA or

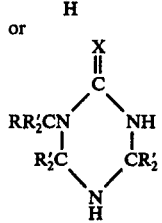           VA wherein R, R' and X are previously described, may also be used to form the compounds of IV and VI, if desired.

Preferred among compounds of formulae III to VI are those wherein R is alkyl, particularly lower alkyl; X is oxygen or sulfur; $R_1$ is alkyl, particularly lower alkyl; and R' is hydrogen or lower alkyl, particularly hydrogen. Of these preferred compounds, those within formulae IV and VI are the more preferred.

Substituted thiadiazine compounds of the formulae:

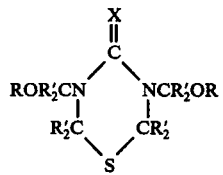           VII or

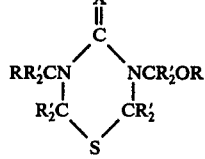           VIII wherein R, R' and X are described above, can be prepared by known reactions such as by reacting a ureido reactant, an aldehyde or ketone, and hydrogen sulfide followed by reaction with an aldehyde or ketone and an alcohol. This preparation is illustrated by the exemplary reaction sequence:

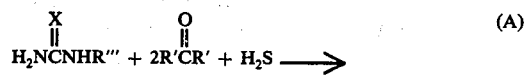           (A)

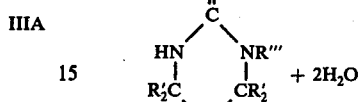

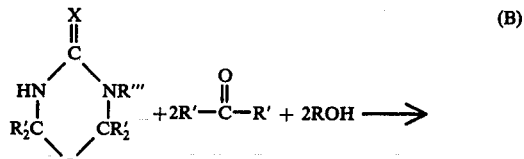           (B)

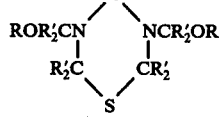           VII or

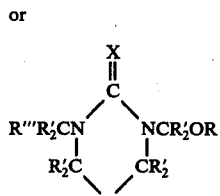           VIII wherein X, R' and R are as above and R''' is hydrogen or R.

Related reactions of ureido compounds, aldehydes and hydrogen sulfide are described in *Journal of Heterocyclic Chemistry*, Vol. 9, pages 231-4, 1972, which is herein incorporated by reference.

Preferred compounds of formulae VII and VIII include those wherein R is alkyl, particularly lower alkyl, R' is hydrogen or lower alkyl, particularly hydrogen and X is oxygen of sulfur, particularly oxygen.

Specific examples of some preferred substituted di- and triazine compounds corresponding to that of reactant (A) are set forth in Table I.

TABLE I

| EXAMPLE | Q | Q' | R' | X | X' |
|---------|---|----|----|---|----|
| AA | $CH_3O-$ | $CH_3O-$ | All H | O | O |
| BB | $n-C_8H_{17}O-$ | $n-C_8H_{17}O-$ | All H | O | O |
| CC | $CH_3O-$ | $CH_3O-$ | All H | S | O |
| DD | $C_2H_5O-$ | $C_2H_5O-$ | All H | O | $=NC_4H_9$ |
| EE | $CH_3O-$ | $CH_3O-$ | All H | S | $=NCH_3$ |
| FF | $CH_3O-$ | $CH_3O-$ | All H | S | S |
| GG | $CH_3-$ | $C_2H_5O-$ | All H | O | O |
| HH | $CH_3O-$ | $CH_3O-$ | All H | =NH | O |
| II | $C_6H_{13}O-$ | $CH_3-$ | All H | $=NC_2H_5$ | O |
| JJ | $C_3H_7-$ | $CH_3O-$ | All H | O | $=NC_4H_8OH$ |
| KK | $C_5H_{11}-$ | $CH_3O-$ | All H | O | O |
| LL | $CH_3O-$ | $CH_3O-$ | All $CH_3-$ | S | O |
| MM | $CH_3O-$ | $C_2H_5O-$ | All H | O | O |
| NN | $C_4H_9O-$ | $C_4H_9O-$ | $CH_3-$; H | O | O |
| OO | $C_6H_{13}O-$ | $C_6H_{13}O-$ | All H | S | $=NC_5H_{10}Cl$ |

TABLE I-continued

| EXAMPLE | Q | Q' | R' | X | X' |
|---|---|---|---|---|---|
| PP | CH₃O— | CH₃O— | All H | O | =N-CH₃ |

Substituted di- and triazine compounds of the formula

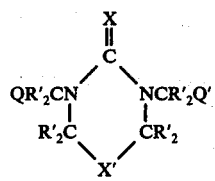  IX wherein X, X' and R' are as hereinbefore stated and one or both of Q and Q' is halogen can be prepared, for instance, by reacting one or more of the compounds of formulae I to VIII with thionyl halides. The thionyl halide reacts to replace one or more hydrocarbyloxy groups of the formula -OR in formulae I-VIII (e.g., methoxy) with a halogen atom. Preferably, in this aspect of the invention herein, Q and/or Q' in formula IX is chloro, bromo or iodo and, more preferably, Q and Q' independently are both selected from the group consisting of chloro, bromo or iodo, particularly chloro or bromo.

Thus, in one method for the preparation of the compounds of formula IX, thionyl halides are reacted with substituted di- or triazine compounds of the formulae:

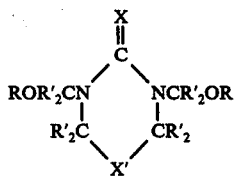  X or

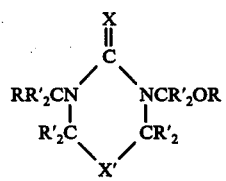  XI wherein X, X', R and R' are as previously stated to yield compounds of the formulae:

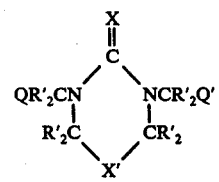  XII or

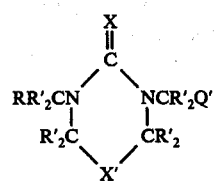  XIII wherein Q and Q' are halo. Of course, in formula XII, only one of Q and Q' need be halogen, and the other can be hydrocarbyloxy.

Preferred compounds within these compounds of formulae XII and XIII include those wherein X is oxygen or sulfur, particularly oxygen; X' is oxygen or sulfur, particularly oxygen; R is alkyl, particularly lower alkyl; R' is hydrogen or lower alkyl, particularly hydrogen; and at least one of Q and Q' is chloro or bromo.

An example of the preparation of such preferred compounds wherein X and X' are oxygen is described in *Liebigs Ann. Chem.* 766, page 58, and following (1972). In the interest of brevity, this article is expressly herein incorporated by reference. It describes, for example, a reaction of a substituted oxadiazine compound with a thionyl chloride while maintaining the temperature between 60° and 70° C. Similarly, other thionyl halides can be reacted with the compounds of formulae X and XI to form the desired halogen-containing substituted di- and triazine compounds of formulae XII or XIII wherein Q and/or Q' is halogen.

Alternatively, the halogen-containing substituted di- and triazine compounds described by formulae XII or XIII can be prepared by starting with, for example, N-methylol or N', N-methylol derivatives of substituted di- and triazine compounds of formulae IX (i.e., Q and-/or Q' is —OH) and thereafter replacing the hydroxy groups with halides. Other methods for preparing the halogen-containing compounds of formulae XII and XIII are apparent to those skilled in the art.

The substituted di- and triazine compounds of (A) are reacted with the one or more mercapto compounds or salts thereof (B) to form the reaction mixtures of this invention. These mercapto compounds of (B) are of the formula ZSY wherein Y is hydrogen, a Group I or an equivalent of Group II metal cation, or an ammonium cation having a total of up to about 20 carbon atoms and Z is selected from the group consisting of groups of the formula:

(1) hydrocarbyl groups of the formula —R" — having from 4 to about 40 carbon atoms;

(2) phosphorus acid groups of the formula:

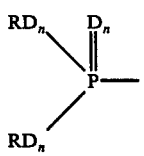

wherein each R is independently hydrocarbyl of up to about 20 carbon atoms, D is oxygen or divalent sulfur; and each n is independently zero or 1;

(3) amido-carbo groups of the formula:

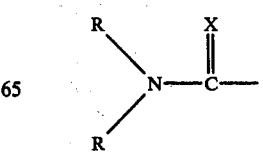

wherein each R is independently hydrocarbyl of up to about 20 carbon atoms; and X is oxygen, divalent sulfur, a =NH or =NR$_1$ wherein R$_1$ is hydrocarbyl of up to about 20 carbon atoms;

(4) hydrocarbyloxycarbo groups and sulfur-containing analogs of the formula:

wherein R is hydrocarbyl of up to about 20 carbon atoms and D is oxygen or divalent sulfur; and (5) mixtures of any two or more of the groups within (1), (2), (3) and/or (4).

Preferred products of (A) and (B) of this invention include those wherein Z is B(1) or B(2), or mixtures of these.

The mercaptans or salts thereof of the formula R"SY are well known. Examples of these materials include primary, secondary, and tertiary mercaptans as well as their respective Group I, Group II metal salts and ammonium salts. Examples of such mercaptans include alkyl mercaptans, cycloalkylmercaptans, arylmercaptans, alkarylmercaptans and aralkylmercaptans and their respective salts. Specific examples of such materials include 1-heptanethiol; 1-decanethiol; 1-eicosanethiol; 4-butylcyclohexanethiol; sodium 2-hexadecanethiolate; potassium 3-(2-cyclohexene-1-yl)-2-methyl-1-propanethiolate; 2-chloro-6-naphthylenethiol; phenylmethylthiol; 12-phenyldodecylthiol; ammonium docosanethiolate; octanethiol; and the calcium salt thereof; 3-decanethiol and the potassium salt thereof; mixed di- and triisobutylene thiols and sodium and potassium salts thereof.

Preferred mercaptans and salts derived from B(1) groups include those wherein R" is alkyl of from 4 to about 20 carbon atoms, more preferably, primary, secondary or tertiary alkyl mercaptans or alkali metal salts thereof having from 8 to about 20 carbon atoms. Examples of these preferred mercaptans include mercaptans formed by treating butylene oligomers as well as propene oligomers with hydrogen sulfide in the presence of catalyst to form the desired mercaptans.

The thiolphosphorus acid and salt groups of B(2) are known. They include tri- and pentavalent acids of the formulae:

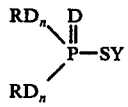

and

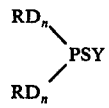

wherein D is oxygen or sulfur; n is zero or 1 and R is a hydrocarbyl group of up to about 20 carbon atoms. Examples of such acids include: (1) Dihydrocarbylphosphinodithioic acids, such as diethylphosphinodithioic acid, corresponding to the formula, (C$_2$H$_5$)$_2$P(S)SH; (2) S-hydrocarbyl hydrogen hydrocarbylphosphonotrithioates, such as S-ethyl hydrogen ethylphosphonotrithioate, corresponding to the formula, (C$_2$H$_5$)(C$_2$H$_5$S)P(S)SH; (3) O-hydrocarbyl hydrogen hydrocarbylphosphonodithioates, such as O-ethyl hydrogen ethylphosphonodithioate, corresponding to the formula, (C$_2$H$_5$)(C$_2$H$_5$O)P(S)SH; (4) Dihydrocarbyl hydrogen phosphorotetrathioates, such as diethyl hydrogen phosphorotetrathioate, corresponding to the formula, (C$_2$H$_5$S)$_2$P(S)SH; (5) O,S-dihydrocarbyl hydrogen phosphorotrithioates, such as O,S-diethyl hydrogen phosphorotrithioate, corresponding to the formula, (C$_2$H$_5$O)(C$_2$H$_5$S)P(S)SH; (6) O,O-dihydrocarbyl hydrogen phosphorodithioates, such as O,O-diethyl hydrogen phosphorodithioate, corresponding to the formula, (C$_2$H$_5$O)$_2$P(S)SH; and (7) the respective trivalent phosphorus analogs (formula 2b) of (1) to (6) as well as respective salts of all of (1) to (7) formed with the metal or ammonium cations of Y.

Preferred compounds of (B) (2) include those of formula 2(a) wherein RD is alkyloxy, aryloxy or alkaryloxy, more preferably alkoxy of up to about 20 carbon atoms; D of

is sulfur; Y is hydrogen or alkali metal; and n is 1.

The carbo-amido groups of B(3) are known. Suitable preparations of compounds containing the B(3) groups can be found in literature reviews such as "The Dithiocarbamates and Related Compounds" by Thorn Lubwig (Elseview Publishing Co., 1962). These thiocarbamates have the formula:

wherein X, Y and R are as previously defined. They include thiolcarbamate salts of the formula:

wherein Y is a Group I or equivalent of Group II metal cation or an ammonium cation and each R is independently hydrocarbyl of up to about 20 carbon atoms, preferably alkyl; dithiocarbamate salts of the formula:

wherein Y and R are as next above; and aminoamidothioic acid derivatives of the formulae:

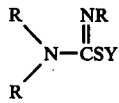

(3) (c) (ii)

wherein each R is hydrocarbyl of up to about 20 carbon atoms and Y is a Group I or an equivalent of a Group II metal cation or an ammonium cation.

Preferred compounds of (B) (3) include those wherein R of B(3) is alkyl of from 1 to about 20 carbon atoms; Y is an alkali metal; and X is oxygen or divalent sulfur, preferably sulfur, i.e., those of formula 3(b). Examples of these thiocarbamate compounds include:

(3) (a) sodium dihexylthiolcarbamate, potassium hexylmethylthiolcarbamate, and ammonium hexadecyloctylthiolcarbamate; (3) (b) sodium didecyldithiocarbamate, potassium dimethyldithiocarbamate, and mixed lithium, potassium and sodium dioctyldithiocarbamates; (3) (c) sodium 1-aminomethanimidothioate (i.e., sodium salt of isothiourea), potassium 1-hexyl-3,3-hexadecylaminomethanimidothioate, and sodium 1-(6-chlorooctadecyl)-3,3 methylpropylaminoethanimidothiate.

(4) The carbo-hydrocarbyl or thiocarbo-hydrocarbyl groups of B(4) are known. The thiocarbonates derived from B(4) groups include compounds of the formulae:

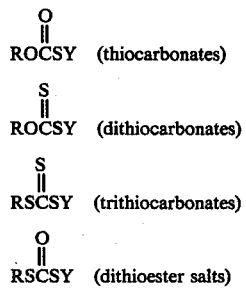

wherein R is hydrocarbyl of up to about 20 carbon atoms, and Y is a Group I or an equivalent of a Group II metal cation or an ammonium cation having up to about 20 carbon atoms.

Preferably, R is alkyl of up to about 20 carbon atoms in (4) (a), (4) (b), (4) (c) and (4) (d) above with such compounds within formulae (4) (a), (4) (b) and (4) (c) being preferred.

Examples of such preferred compounds include 4(a) potassium ethylthiocarbonate, sodium octadecylthiocarbonate and sodium phenylbutylthiocarbonate; 4(b) sodium octylxanthate, ammonium octadecylxanthate, and calcium bis(phenylmethylxanthate); 4(c) ammonium hexyltrithiocarbonate, sodium eicosyltrithiocarbonate, and potassium 1-methyldecyltrithiocarbonate.

The Y group of ZSY is selected from the group consisting of hydrogen, a Group I metal, or an equivalent of a Group II metal (divalent metals have two equivalents in contrast to monovalent metals which have one equivalent) or an ammonium cation. Normally, the Group I metals are alkali metals such as sodium or potassium and the Group II metals are alkaline earth metals such as calcium or barium. The ammonium cation can be, for example, quaternary ammonium cations having a total carbon content of up to about 20. Usually Y will be alkali metal or hydrogen.

Mixtures of compounds containing two or more B(1), B(2), B(3), and/or B(4) groups are, of course, useful herein, especially when the reaction is conducted under basic conditions. Thus, the mixtures may be, for example, two compounds each having different B(1) groups as well as two compounds, one having a B(1) group and another having a B(2) group.

The di- and triazines of (A) preferably react, when either or both of Q and Q' are hydrocarbyloxy, with the mercapto compounds in acid form, e.g., Y is hydrogen. Alternatively, when either or both of Q and Q' are halogen, then the salts (preferably metal) of (B) are employed. If one of Q and Q' is halogen and the other hydrocarbyloxy, then either the acid or salt form of (B) may be employed. However, inasmuch as the mercapto compounds of B(3) and B(4) are often considerably less stable under acid conditions, B(3), B(4) or mixtures containing these will normally be used in salt form, preferably as alkali metal salts, and when at least one of Q and Q' is halogen.

The use of an acid catalyst facilitates reaction of the di- and triazines of (A) (wherein either or both of Q and Q' are hydrocarbyloxy) and weakly acidic compounds of (B) wherein Y is hydrogen, i.e., the B(1) mercaptans. When B(2) acids (i.e., Z is B(2) and Y is hydrogen) are used in such situations, the acid catalyst is normally unnecessary for a desirable reaction rate.

Useful acid catalyst include strong acids such as mineral acids (e.g., hydrogen chloride, sulfuric acid and the like) and organic acids such as paratoluene sulfonic acid and trimethylsulfonic acid.

The reaction of the di- and triazine compound of (A) with the mercapto compound of (B) generally is conducted at atmospheric pressure, although high or lower pressures may be employed. The reaction of (A) and (B) is normally conducted within a temperature range of 20° C. to 250° C., preferably 50° C. to 150° C., although temperatures up to the decomposition temperatures of the product or reactant can be employed, if desired. The reaction may be conducted in the presence, or absence, of added media, e.g., a substantially inert solvent or diluent, if desired.

When the reaction is conducted in the presence of an added reaction media, the total amount of the added media is not critical. Ordinarily, the added media will comprise from about 10% to about 80%, preferably, about 30% to about 70% by weight of a reaction mixture based upon the total weight of the reactants and reaction media in the reaction mixture. Usually this media will be, "substantially inert", i.e., a material which does not materially interfere with the reaction or react in any significant amount under the conditions of the reaction as described and exemplified herein. It can be, however, excess of (A) or (B) acting as diluent.

Selection of suitable diluents or solvents is within the skill of the art and are usually substantially, normally liquid, organic compounds. Such materials include aliphatic hydrocarbons, aromatic ring chlorides, ethers, and the like such as heptane, octane, dodecane, cyclohexane, mineral oil, kerosene, chlorobenzene, 1,4-dioxane, n-propyl ether, methyl n-amyl ether and mixtures of two or more of these.

The reaction may be carried out, for example, by simply mixing one or more di- and triazine compounds of (A) with one or more mercapto compounds in the presence or absence of suitable additional reaction media at room temperature conditions. To this mixture may be added the acid catalyst, as desired, and the mixture may be heated to accelerate the reaction, if desired.

The reactants (A) and (B), for example, can be admixed in a wide range of molar ratios (e.g., about 1:10 to 10:1), for reaction, but desirably the mercapto compounds of (B) are reacted at a level of about one-half to about 4 moles of mercapto compound (B) per total moles of di- or triazine compounds of (A). If either Q or Q' is hydrocarbyl, then a molar ratio within a range of about 1:2 to 2:1 is desirable, although greater levels of mercapto compounds (B) or di- and triazine compounds (A) may be used to accelerate the reaction, and the unreacted reactants, if any, removed, if desired, during a separation step.

The separation step, if desired can be by any conventional means. For example, filtration and distillation techniques are useful. Further, it may be desirable to remove at least some of any excess acidic catalyst and this may be accomplished according to methods known in the art such as neutralization, aqueous washing and filtration through diatomaceous earth.

While not intending to be limited by any theory as to the nature of the compounds which are prepared, the reaction mixture derived from the reaction of (A) with (B) pursuant to this invention is believed, in certain circumstances and at least in part, to contain compounds corresponding to the formulae:

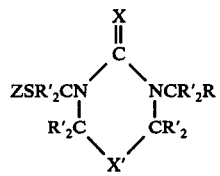   XX or

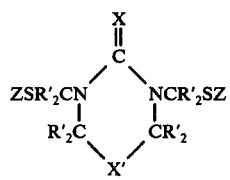   XXX wherein X, X', R', R and Z are as described hereinbefore.

However, since the utility of this invention is not dependent upon formation of compounds of a particular structure, and, moreover, since the reaction product of this invention may also contain a mixture of materials not readily identifiable, this invention is described herein in terms of the reaction mixture made by reacting (A) with (B). While this reaction mixture may be used per se in lubricating and fuel compositions it is usual commercial practice to at least filter and remove any volatiles from such reaction mixtures before addition to a fuel or lubricant. Accordingly, all weights and percentages herein are based on the weight of the filtered reaction mixture, absent any solvent or diluent.

In a further aspect of this invention, the reaction mixture made by reacting (A) with (B) as described hereinbefore is sulfurized to provide an increase in sulfur content of the resulting sulfur-containing reaction mixture. This increase is at least about 0.5% (preferably about 1% to about 5%) by weight based upon the total weight of the reaction mixture (exclusive of any solvent or diluent) derived from reacting (A) with (B). This sulfurization may be accomplished according to sulfurization methods known in the art but is preferably conducted by heating elemental sulfur or a sulfur-producing compound (e.g., $Na_2S$) with the reaction mixture of (A) and (B) to a temperature of up to less than the decomposition temperature of product or reactant, desirably about 20° to about 250° C., more preferably 50° C. to 200° C. The amount of sulfur reacted will normally be from about 1:20 to about 10:1 by weight (preferably 1:10 to 2:1) based on the weight of the reaction mixture of (A) and (B), exclusive of any solvent or diluent. The resultant sulfurized product can then be separated from the reaction mass by conventional techniques e.g., vacuum distillation and filtering. Of course, excess elemental sulfur or sulfur-producing compounds can be removed, if desired, by conventional techniques such as filtration. The sulfurized mixture is especially useful as an EP agent and antioxidant in lubricants.

The following examples illustrate this invention, but are not intended as limiting thereof. In all the examples, as well as elsewhere in the specification and appended claims, all percentages are expressed as percent by weight and all parts are expressed as parts by weight, unless otherwise indicated. Likewise, all temperatures are expressed in degrees centigrade (° C.) unless otherwise indicated, and all pressures are expressed in pounds per square inch unless otherwise indicated.

EXAMPLE 1

A mixture of urea (60 grams, 1.0 mole), formaldehyde (480 grams of a 37.7% formalin solution) and 10 ml of a 40% sodium hydroxide solution is held at 60° C. for 2 hours. The pH of the reaction mixture is adjusted to 5 with approximately 5 ml formic acid and then the solution is stripped to 60° C. under a vacuum of 25 torr. To the syrupy residue is added methanol (576 grams, 18.0 moles) and 16.7 ml of a 37.5% hydrochloric acid solution and the mixture is kept below 30° C. for 1 hour using a water bath. The material is neutralized with a 40% sodium hydroxide solution, stripped to 40° C. under a vacuum of 5 torr and then filtered through diatomaceous earth. The filtrate contains the desired, 3,5-dimethoxymethyl-4-oxotetrahydro-1,3,5-oxadiazine, (i.e., formula I wherein X and X' are oxygen; R is methyl; and R' is hydrogen) having a %N of 12.9.

EXAMPLE 2

The procedure of Example 1 is followed except thiourea (76 grams, 1.0 mole) is substituted for the urea and propionaldehyde (232 grams, 4.0 moles) is substituted for the formalin solution. The filtrate contains the desired product (i.e., X is sulfur; R' is ethyl; and X' and R are as in Example 1).

EXAMPLE 3

The procedure of Example 1 is followed except guanidine hydrochloride (95.5 grams, 1.0 mole) is substituted for the urea, methylethyl ketone (288 grams, 4.0 moles) is substituted for the formalin solution and 110 ml. of the sodium hydroxide is used. The filtrate is the desired product (i.e., X is =NH; R' is ethyl; and X' and R are as in Example 1).

EXAMPLE 4

Dodecylthiol (199 grams), the filtrate of Example 1 (95 grams) and 1.5 ml of a 37.5% hydrochloric acid solution is held at 60° C. for 3 hours. After standing about 72 hours at 25° C., the material is held at 80°–90° C. for 10 hours. The material is added to 500 ml textile spirits (an aliphatic petroleum naphtha having a distillation range of 63°–79° C. at 760 torr), washed with water, neutralized with a potassium carbonate solution and washed again with water, then dried with magnesium sulfate. The material is filtered, the filtrate is stripped to 100° C. under a vacuum of 25 torr and the residue is filtered through diatomaceous earth. The filtrate contains the desired product having a %N of 4.77 and a %S of 12.6.

EXAMPLE 5

Sulfur flowers (10.7 grams) and the filtrate of Example 4 (87.3 grams) is slowly heated to 120° C. whereupon a homogeneous solution is formed. The solution is held at 160°–170° C. for 1.5 hours, cooled to 100° C. and then stripped under a vacuum of 25 torr and filtered through diatomaceous earth. The filtrate contains the desired sulfurized product having a %N of 3.92 and %S of 19.6.

EXAMPLE 6

The filtrate of Example 1 (190 grams) and the reaction product of 4 moles tetrapropenyl phenol with 1 mole $P_2S_5$ having a %S of 9.80, %P of 4.75 (i.e., formula B(2) (a) wherein Y is hydrogen, $RD_n$ is propenylphenoxy, and D is sulfur) and a neutralization number to bromophenolblue of 87.5 acid (1280 grams) is held at 60° C. for 0.5 hour. A water aspirator vacuum is applied and the material is slowly heated to 100° C. and held for 1 hour (the vacuum was 34 torr at the end). The residue contains the desired product having a %N of 1.94, a %S of 8.98, a %P of 4.07 and a neutralization number to phenolphthalein of 6.

EXAMPLE 7

Armeen-O, being primarily oleoylamine and being available from Armour Chemical Company, (556 grams) is slowly added to a mixture of urea (144 grams) and 500 ml dimethylformamide at 100° C. The reaction mixture is held at 150° C. for 6 hours and then stripped to 150° C. under a vacuum of 20 torr. The residue is filtered hot through diatomaceous earth and the filtrate contains the desired

$$C_{18}H_{36}NHCNH_2.$$

EXAMPLE 8

Formalin (175 grams of a 37.7% solution), the filtrate of Example 7 (160 grams) dissolved in tetrahydrofuran (THF) (200 grams) and 5 ml of a 40% sodium hydroxide solution is held at 60° C. for 6 hours. The pH of the solution is adjusted to 5 with formic acid. The solution is stripped to 60° C. under a vacuum of 24 torr. Methanol (288 grams, 9.0 moles) and 8.5 ml of a 37.5% hydrochloric acid solution is added to the residue and held for 18 hours at room temperature. The material is neutralized with a 40% sodium hydroxide solution and stripped to 40° C. under a vacuum of 5 torr. The residue is filtered hot through diatomaceous earth. The filtrate contains the desired product (A) (i.e., formula XIII wherein R is $C_{17}H_{34}$; Q' is $CH_3O$—; X is oxygen; X' is oxygen, R' is hydrogen).

EXAMPLE 9

Thionyl chloride (30 grams) in 25 ml toluene is added to a solution of 25 ml toluene and the filtrate of Example 8 (102 grams, 0.25 mole) dropwise at 60°–65° C. over a 0.25 hour period. The material is held at 70°–80° C. for 1 hour and then stripped to 110° C. under a vacuum of 40 torr. The residue is filtered hot through diatomaceous earth. The filtrate contains the desired monohalogenated product having a %N of 7.57 and a %Cl of 5.43 wherein a chloro atom replaces the methoxy radical.

EXAMPLE 10(a)

Carbon disulfide (76 grams, 1.0 mole) is added during a 1.5-hour period to a mixture of di-n-butyl amine (129 grams, 1.0 mole), 160 grams of a 50% sodium hydroxide solution and 175 ml water while controlling the exothermic reaction so that the final temperature is 60°–65° C. The material is stripped to 85° C. under a vacuum of 15 torr. The product is the desired di-n-butyl dithiocarbamate sodium salt (i.e., formula (B) (3) (b) wherein R is n-butyl, X is sulfur).

EXAMPLE 10(b)

Sodium di-n-butyl dithiocarbamate prepared in Example 10(a) (227 grams, 1.0 mole) is slowly added to the filtrate of Example 9 (412 grams, 1.0 mole) dissolved in 1000 grams of toluene over a temperature range of 55°–80° C. during a 3-hour period. The material is filtered and then stripped to 80° C. under a vacuum of 30 torr and filtered again through diatomaceous earth. The filtrate contains the desired product.

EXAMPLE 11

The procedure of Example 10(b) is followed except potassium ethylthiocarbonate (144 grams) (i.e., B(4) (a) wherein R is ethyl; D is oxygen and Y is potassium) is substituted for the sodium di-n-butyldithiocarbamate.

EXAMPLE 12

The procedure of Example 10(b) is followed except potassium ethyl xanthate (ie.., B(4) (b) wherein R is ethyl; D is oxygen, sulfur; and Y is sodium) (160 grams) is substituted for the sodium di-n-butyldithiocarbamate.

EXAMPLE 13

The procedure of Example 10(b) is followed except potassium ethyl trithiocarbonate (i.e., B(4) (c) wherein D is sulfur; Y is potassium and R is ethyl) (176 grams) is substituted for the sodium di-n-butyldithiocarbamate.

EXAMPLE 14

The procedure of Example 10(b) is followed except potassium ethyl dithiocarbonate (i.e., B4(d) wherein D is sulfur, oxygen; R is ethyl and Y is potassium) (148 grams) is substituted for the sodium di-n-butyldithiocarbamate.

EXAMPLE 15

The procedure of Example 9 is followed except 59.5 grams of thionyl chloride is used and the filtrate of Example 1 (47.5 grams, 0.25 equivalent) is substituted for the filtrate of Example 8. The filtration step is omitted as the solid residue from stripping is the product. The residue contains the halogenated product whereby the methoxy radicals are replaced by chloro atoms.

EXAMPLE 16

The procedure of Example 10(b) is followed except 56.8 grams of sodium di-n-butyldithiocarbamate and 160 grams of sodium salt of the reaction product of tetrapropenylphenol with one mole of $P_2S_5$ is used and the residue of Example 15 (49.8 grams) is substituted for the filtrate of Example 9.

EXAMPLE 17(a)

Methylamine (295 grams of a 21% aqueous solution) is added to dimethylolurea (243 grams) dissolved in 340 grams water. The solution is held at 75° C. for 2 hours, then filtered and cooled. The desired product is recovered having a %N of 36.6.

EXAMPLE 17(b)

The product prepared in Example 17(a) (40 grams, 2.88 moles), formalin (63 grams of a 37% solution) and 1.9 grams barium hydroxide are held at 70°-80° C. for 0.25 hour and then concentrated to about 80 grams of a viscous syrup under reduced pressure at 50° C. Methanol (280 grams, 8.75 moles) containing 2.7 grams of a 37.5% hydrochloric acid solution is added and the mixture is allowed to stand for two hours. After neutralizing the hydrochloric acid with sodium carbonate, the excess methanol is evaporated and the residue dissolved in chloroform. The insoluble material is filtered off and the solvent removed by distillation. The residual filtrate is the desired product (i.e., formula VI wherein X is oxygen; $NR_1$ is $=NCH_3$; R is $CH_3—$; R' is hydrogen).

EXAMPLE 18

The procedure of Example 4 is followed except the filtrate of Example 17(b) (203 grams, 1.0 mole) is substituted for the filtrate of Example 1.

EXAMPLE 19(a)

Dimethylolurea (243 grams) and 5 grams para-toluene sulfonic acid dissolved in 340 grams of water is refluxed while hydrogen sulfide gas is passed through. The solution is then stripped to 60° C. under a vacuum of 25 torr.

EXAMPLE 19(b)

The product prepared in Example 19(a) is treated as in Example 17(b) to form the desired 3,5-dimethoxy-4-oxotetrahydrothiadiazine.

EXAMPLE 20

The procedure of Example 9 is followed except the filtrate of Example 19(b) (25.8 grams, 0.125 mole) is substituted for the filtrate of Example 8.

EXAMPLE 21

The filtrate of Example 20 (21.5 grams, 0.10 mole) is reacted with the filtrate of Example 10(a) (45.4 grams, 0.20 mole) according to the procedure in Example 10(b). The filtrate is the desired product.

EXAMPLE 22

A mixture of hexadecylthiol (132 grams) and the reaction product of 4 moles of tetrapropenyl phenol with 1 mole of $P_2S_5$ (640 grams) is reacted with the filtrate of Example 1 (95 grams) according to the procedures of Example 6 except that hydrochloric acid is used as a catalyst.

EXAMPLE 23

A mixture of potassium octadecylthiolate (160 grams) and sodium dihexyl dithiocarbamate (200 grams) is reacted with the residue prepared as in Example 15 (100 grams) according to the procedures of Example 10(b).

EXAMPLE 24

A mixture of Examples AA (75 grams) and PP (100 grams) is reacted according to the procedures of Example 4.

EXAMPLE 25

In this Example, AA and BB are replaced in Example 24 with Example FF (160 grams).

EXAMPLE 26

In this Example, the filtrate of Example 24 is sulfurized according to the procedures of Example 5.

The compositions (i.e., reaction mixtures of (A) and (B), optionally sufurized) of this invention are soluble and/or stably dispersible in the normally liquid media (e.g., oil, fuel, etc.) in which they are intended to function. Thus, for example, reaction mixtures formed by reacting (A) with (B), optionally sulfurized, intended for use in oils are oil-soluble and/or stably dispersible in an oil in which they are to be used. The terminology "oil-soluble" as used herein and in the appended claims does not necessarily mean that the compositions are miscible or soluble in all proportions in all oils. Rather, it is intended to mean that the composition is soluble in an oil (mineral, synthetic, etc.) in which it is intended to function to an extent which permits the solution to exhibit one or more of the desired properties. Similarly, it is not necessary that such "solutions" be true solutions in the strict physical or chemical sense. They may instead be micro-emulsions or colloidal dispersions which, for the purpose of this invention, exhibit properties sufficiently close to those of true solutions to be, for practical purposes, interchangeable with them within the context of this invention.

The terminology "stably dispersible in the normally liquid media" as used herein and in the appended claims is intended to mean a composition (e.g., a single additive or a mixture of two or more additives. etc.) which is capable of being dissolved or dispersed in a given medium to an extent which allows it to function in its intended manner. Thus, for example, where a composition of this invention is used in an oil, it is sufficient that the composition be capable of being suspended in the oil in an amount sufficient to enable the oil to possess one or more of the desired properties imparted to it by the suspended composition. Such suspension of the compositions can be achieved in various conventional ways. For example, in constantly circulating oil or oil in splash lubricating systems, physical agitation can keep the compositions suspended in oil. Likewise, conventional dispersants (such as the acylated nitrogen dispersants disclosed in U.S. Pat. No. 3,219,666) often found in lubricating oils and fuels promote the stable dispersion or suspension of the composition. In any event, the intended compositions will be "soluble" or "stably dispersible" in the normally liquid media in which they will be used in at least the minimum concentrations set forth elsewhere herein. Thus, the terminology "soluble" and "stably dispersible" is used in a conventional manner and will be understood by those of ordinary skill in the art.

As previously indicated, the reaction products of (A) and (B), optionally sulfurized, of this invention are useful as additives for lubricants, in which they function primarily as oxidation inhibitors, anti-wear agents, and extreme pressure (EP) agents.

As lubricating oil additives, the reaction mixtures comprise from about 0.01% to about 20%, preferably from about 0.1% to about 10%, by weight based upon the total weight of the lubricating oil and one or more additives combined. As before, these weight percents are based upon the filtered product absent diluent or solvent.

The lubricating oil compositions of this invention are based on natural and synthetic lubricating oils and mixtures thereof. These lubricants include crankcase lubricating oils for spark-ignited and compression-ignited internal combustion engines, such as automobile and truck engines, marine and railroad diesel engines, and the like. Automatic transmission fluids, transaxle lubricants, gear lubricants, metal-working lubricants, hydraulic fluids and other lubricating oil and grease compositions can also benefit from the incorporation therein of the compositions of this invention.

Natural oils include animal oils and vegetable oils (e.g., castor oil, lard oil) as well as mineral lubricating oils such as liquid petroleum oils and solvent-treated or acid-treated mineral lubricating oils of the paraffinic, naphthenic or mixed paraffinic-naphthenic types. Oils of lubricating viscosity derived from coal or shale are also useful base oils. Synthetic lubricating oils include hydrocarbon oils and halo-substituted hydrocarbon oils such as polymerized and interpolymerized olefins (e.g., polybutylenes, polypropylenes, propylene-isobutylene copolymers, chlorinated polybutylenes, etc.); poly(1-hexenes, poly(1-octenes), poly(1-decene), etc. and mixtures thereof; alkylbenzenes (e.g., dodecylbenzenes, tetradecylbenzenes, dinonylbenzenes, di-(2-ethylhexyl)-benzenes, etc.); polyphenyls (e.g., biphenyls, terphenyls, alkylated polyphenyls, etc.); alkylated diphenyl ethers and alkylated diphenyl sulfides and the derivatives, analogs and homologs thereof and the like.

Alkylene oxide homopolymers and interpolymers and derivatives thereof where the terminal hydroxyl groups have been modified by esterification, etherification, etc. constitute another class of known synthetic lubricating oils. These are exemplified by the oils prepared through polymerization of ethylene oxide or propylene oxide, the alkyl and aryl ethers of these polyoxyalkylene polymers (e.g., methylpolyisopropylene glycol ether having an average molecular weight of 1000, diphenyl ether of polyethylene glycol having a molecular weight of 500–1000, diethyl ether of polypropylene glycol having a molecular weight of 1000–1500, etc.) or mono- and polycarboxylic esters thereof, for example, the acetic acid esters, mixed $C_3$–$C_8$ fatty acid esters, or the $C_{13}$ Oxo acid diester of tetraethylene glycol.

Another suitable class of synthetic lubricating oils comprises the esters of dicarboxylic acids (e.g., phthalic acid, succinic acid, alkyl succinic acids, alkenyl succinic acids, maleic acid, azelaic acid, suberic acid, sebacic acid, fumaric acid, adipic acid, linoleic acid dimer, malonic acid, alkyl malonic acids, alkenyl malonic acids, etc.) with a variety of alcohols (e.g., butyl alcohol, hexyl alcohol, dodecyl alcohol, 2-ethylhexyl alcohol, ethylene glycol, diethylene glycol monoether, propylene glycol, etc.). Specific examples of these esters include dibutyl adipate, di(2-ethylhexyl)sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, the complex ester formed by reacting one mole of sebacic acid with two moles of tetraethylene glycol and two moles of 2-ethylhexanoic acid and the like.

Esters useful as synthetic oils also include those made from $C_5$ to $C_{12}$ monocarboxylic acids and polyols and polyol ethers such as neopentyl glycol, trimethylol propane, pentaerythritol, dipentaerythritol, tripentaerythritol, etc.

Silicon-based oils such as the polyalky-, polyaryl-, polyalkoxy-, or polyaryloxy-siloxane oils and silicate oils comprise another useful class of synthetic lubricants (e.g., tetraethyl silicate, tetraisopropyl silicate, tetra-(2-ethylhexyl)silicate, tetra-(4-methylhexyl)silicate, tetra(p-tert-butylphenyl)silicate, hexyl-(4-methyl-2-pentoxy)disiloxane, poly(methyl)siloxanes, poly(methylphenyl)siloxanes, etc.). Other synthetic lubricating oils include liquid esters of phosphorus-containing acids (e.g., tricresyl phosphate, trioctyl phosphate, diethyl ester of decane phosphonic acid, etc.), polymeric tetrahydrofurans and the like.

Unrefined, refined and rerefined oils, either natural or synthetic (as well as mixtures of two or more of any of these) of the type disclosed hereinabove can be used in the lubricant composition of the present invention. Unrefined oils are those obtained directly from a natural or synthetic source without further purification treatment. For example, a shale oil obtained directly from retorting operations, a petroleum oil obtained directly from primary distillation or ester oil obtained directly from an esterification process and used without further treatment would be an unrefined oil. Refined oils are similar to the unrefined oils except they have been further treated in one or more purification steps to improve one or more properties. Many such purification techniques are known to those of skill in the art such as solvent extraction, secondary distillation, acid or base extraction, filtration, percolation, etc. Rerefined oils are obtained by processes, similar to those used to obtain refined oils, applied to refined oils which have been already used in service. Such rerefined oils are also known as reclaimed or reprocessed oils and often are additionally processed by techniques directed to removal of spent additives and oil breakdown products.

The reaction mixtures of this invention can be used alone or in combination with other lubricant additives such as dispersants, detergents, antifoam agents, corrosion inhibitors, viscosity modifiers, other extreme pressure agents, antiwear agents and antioxidants and the like.

These additional additives are well known in the art and a brief survey of conventional additives for lubricating compositions is contained in the publications, LUBRICANT ADDITIVES, C. V. Smalheer and R. Kennedy Smith, published by Lezius-Hiles Co., Cleveland, Ohio, 1967 and LUBRICANT ADDITIVES, M. W. Ranney, published by Noyes Data Corp., Park Ridge, N.J., 1973, which are herein incorporated by reference.

The ash-containing detergents are well known neutral and basic alkali or alkaline earth metal salts of sulfonic acids, carboxylic acids or organophosphorus-containing acids. These phosphorus-containing acids are characterized by at least one direct carbon-to-phosphorus linkage, and can be prepared by steam-treating an olefin polymer, i.e., polyisobutylene, with a phosphorizing agent such as phosphorus trichloride, phosphorus heptasulfide, phosphorus pentasulfide, phosphorus trichloride and sulfur, white phosphorus and a sulfur halide, or phosphorothioic chloride. When used as an ash-containing detergent, the most commonly used salts of these acids are the sodium, potassium, lithium, calcium, magnesium, strontium, and barium salts. The calcium and barium salts are used more extensively than the others. The "basic salts" are those metal salts known in the art wherein the metal is present in a stoichiometrically larger amount than that necessary to neutralize the acid. The calcium and the barium overbased petrosulfonic acids are typical examples of such basic salts. The ashless dispersants are also a well known class of materials used as additives for lubricating oils and fuels. They are particularly effective as dispersants at low temperatures. The hydrocarbon-substituted succinic acids and their derivatives can be used as stabilizing agents in the preparation of the lubricant compositions of this invention and are representative of the dispersants. These dispersants include products obtained by the reaction of the $C_{30}$ or greater hydrocarbon-substituted succinic acid compounds and alkylene polyamines or polyhydric alcohols, which can be further post-treated with materials such as boric acids, metal compounds, etc.

Pour point depressing agents are illustrated by the polymers of ethylene, propylene, isobutylene, and poly-(alkylmethacrylates). Anti-foam agents include polymeric alkyl siloxanes, poly-(alkyl methacrylates), copolymers of diacetone acrylamide and alkyl acrylates or methacrylates, and the condensation products of alkyl phenol with formaldehyde and an amine. Viscosity index improvers include, polymerized and copolymerized alkyl methacrylates and polyisobutylenes.

Other extreme pressure agents, corrosion-inhibiting agents, and oxidation-inhibiting agents, are exemplified by chlorinated aliphatic hydrocarbons, such as chlorinated wax; organic sulfides and polysulfides; such as benzyl disulfide, bis-(chlorobenzyl)disulfide, dibutyl tetrasulfide, sulfurized sperm oil, sulfurized methyl ester of oleic acid, sulfurized alkyl phenol, sulfurized dipentene, sulfurized terpene, and sulfurized Diels-Alder adducts; phosphosulfurized hydrocarbons, such as the reaction product of phosphorus sulfide with turpentine or methyl oleate; phosphorus esters such as the dihydrocarbon and trihydrocarbon phosphites, i.e., dibutyl phosphite, diheptyl phosphite, dicyclohexyl phosphite, pentylphenyl phosphite, dipentyl phenyl phosphite, tridecyl phosphite, distearyl phosphite, and polypropylene substituted phenyl phosphite; metal thiocarbamates, such as zinc dioctyldithiocarbamate and barium heptylphenol dithiodicarbonate; Group II metal salts of phosphorodithioic acids, such as zinc dicyclohexyl phosphorodithioate, and the zinc salt of a phosphorodithioic acid.

The reaction mixture of (A) and (B), optionally sulfurized, can also be used in normally liquid fuels. Usually, when used as an additive for fuels, these reaction mixtures, exclusive of solvents and diluents, will comprise from about 0.0001% to about 1% by weight (preferably 0.001% to about 0.2%) of the total weight of the final fuel.

The fuel compositions of the present invention contain a major proportion of a normally liquid fuel, usually a hydrocarbonaceous petroleum distillate fuel such as aviation or motor gasoline as defined by ASTM Specification D-439-73 and diesel fuel or fuel oil as defined by ASTM Specification D-396. Normally liquid fuel compositions comprising nonhydrocarbonaceous materials such as alcohols, ethers, organo-nitro compounds and the like (e.g., methanol, ethanol, diethyl ether, methyl ethyl ether, nitromethane) are also within the scope of this invention as are liquid fuels derived from vegetable or mineral sources such as corn, alfalfa, shale and coal. Normally liquid fuels which are mixtures of one or more hydrocarbonaceous fuels and one or more non-hydrocarbonaceous materials are also contemplated. Examples of such mixtures are combinations of gasoline and ethanol, and diesel fuel and ether. Particularly preferred is gasoline, that is, a mixture of hydrocarbons having an ASTM boiling point of about 60° C. at the 10% distillation point to about 205° C. at the 90% distillation point.

The fuel compositions of this invention can contain, in addition to the reaction products of (A) with (B), optionally sulfurized, of this invention, other additives which are well known to those of skill in the art. These can include anti-knock agents such as tetra-alkyl lead compounds, lead scavengers such as halo-alkanes (e.g., ethylene dichloride and ethylene dibromide), deposit preventors, antioxidants such as 2,6-di-tertiary-butyl-4-methylphenol, rust inhibitors, such as alkylated succinic acids and anhydrides, bacteriostatic agents, gum inhibitors, metal deactivators, demulsifiers, upper cylinder lubricants, anti-icing agents and the like.

In certain preferred fuel compositions of the present invention, the afore-described reaction products of (A) with (B), optionally sulfurized are combined with an ashless dispersant in gasoline. Such ashless dispersants are preferably esters of a mono- or polyol and a high molecular weight mono- or polycarboxylic acid acylating agent containing at least 30 carbon atoms in the acyl moiety. Such esters are well known to those of skill in the art. See, for example, French Pat. No. 1,396,645, British Patent Nos. 981,850 and 1,055,337 and U.S. Pat. Nos. 3,255,108; 3,311,558; 3,331,776; 3,346,354; 3,522,179; 3,579,450; 3,542,680; 3,381,022; 3,639,242; 3,698,428; 3,708,522; and British Patent Specification No. 1,306,529. These patents are expressly incorporated herein by reference for their disclosure of suitable esters and methods for their preparation. Generally, the weight ratio of the reaction mixtures of (A) with (B), optionally sulfurized, of this invention, exclusive of any solvent or diluent, to the aforesaid ashless dispersants is about 0.1 to about 10.0, preferably about 1 to about 10 parts of the reaction mixture, optionally sulfurized, to 1 part ashless dispersant. In still another embodiment of this invention, the inventive additives are combined in an analogous manner with ashless dispersants which are Mannich condensation products formed from substituted phenols, aldehydes, polyamines, and substituted pyridines. Such condensation products are described in U.S. Pat. Nos. 3,649,659; 3,558,743; 3,539,633; 3,704,308; and 3,725,277.

Additive concentrates of the reaction mixtures of this invention are conveniently used for transporting, mixing, formulating, etc. the reaction mixtures of this invention with lubricating oils and other additives. These additive concentrates are conventionally employed in the art for such purposes and comprise from about 20% to about 80% by weight of the reaction mixture of (A) with (B), optionally sulfurized, of this invention, optionally, admixed with other additives, and from about 80% to about 20% by weight of a normally liquid diluent or carrier, said percentages based on the total additive concentrate. The weight of the reaction mixture is exclusive of any solvent of diluents. The liquid diluent or carrier is usually one or more materials which solubilize the additive compositions, examples of which are hydrocarbons, chlorinated hydrocarbons, ethers and the like.

EXAMPLE A

A lubricating composition suitable for use as an automatic transmission fluid (ATF) is prepared using an ATF mineral base oil and, as additives, by weight, 4.0% of a mixed ester of a styrene-maleic anhydride copolymer reacted with a nitrogen-containing compound (prepared as in U.S. Pat. No. 3,702,300); 3.0% of the reaction product of a polyisobutenyl-substituted succinic anhydride and commercial tetraethylene pentamine (prepared as in U.S. Pat. No. 3,172,892); 1.0% of the reaction product of a polyisobutenyl-substituted succinic anhydride, commercial tetraethylene pentamine and boric acid (prepared as in U.S. Pat. No. 3,254,025); 0.2% of a commercial diphenylamine-based oxidation inhibitor; 0.5% of a conventional friction modifier based on polyoxyethylene (2) tallowamine; 0.1% of a di(4-methyl-secondary amyl) phosphite; 3.0% of a commercial seal sweller; 0.02% of a conventional silicone-based antifoam agent; and 2.0% of the filtrate of Example 4.

EXAMPLE B

A lubricating composition suitable for use as a gear lubricant is prepared using an SAE 90 mineral base oil and, as additives, by weight 1.3% of the reaction product of di(4-methyl-secondary amyl) phosphite and a tertiary alkyl primary amine wherein the alkyl group is derived from a $C_{12}$ to $C_{14}$ hydrocarbon mixture; 0.5% of an oleamide, linoleamide mixture; 0.2% of Amoco 150, a commercial copper deactivator; 0.08% of a commercial antifoam agent derived from a polyacrylate; and 9.6% of the filtrate of Example 5.

EXAMPLE C

A lubricating composition suitable for use as a crankcase lubricant is prepared using an SAE 10W-40 mineral oil and, as additives, by weight, 8.5% of a polyacrylate viscosity modifier; 6.0% of the reaction product of a polyisobutenyl-substituted succinic anhydride and pentaerythritol (prepared as in U.S. Pat. No. 3,522,179); 1.5% of a commercial mixed hindered phenol antioxidant; 60 ppm of a commercial silicone-based antifoam agent; and 2.0% of the filtrate of Example 6.

EXAMPLE D

In this example, the filtrate of Example 4 in Example A is replaced, on an equal weight basis, with the filtrate of Example 10(b).

EXAMPLE E

In this example, the filtrate of Example 5 in Example B is replaced with 3.0% of the filtrate of Example 18.

EXAMPLE F

In this example, the filtrate of Example 6 in Example C is replaced on an equal weight basis, with the filtrate of Example 21.

EXAMPLE G

Diesel fuel containing 0.02% of the filtrate of Example 4.

EXAMPLE H

Diesel fuel containing 0.01% of the filtrate of Example 18 and 0.005% of the filtrate of Example 10(b).

What is claimed is:

1. A composition of matter which is the reaction mixture made by reacting
   (A) at least one of the substituted di- and tri-azine compounds of the formula:

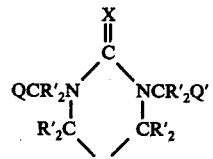

wherein Q and Q' are each independently selected from the group consisting of halo, hydrocarbyloxy of the formula —OR and hydrocarbyl of the formula —R, wherein each R independently contains up to about 20 carbon atoms, with the proviso that at least one of Q and Q' is hydrocarbyloxy or halo; X and X' are each independently selected from the group consisting of oxygen, divalent sulfur, =NH, or =NR$_1$ wherein R$_1$ is as R above; and each R' is independently hydrogen or hydrocarbyl of up to about 10 carbon atoms; with
   (B) at least one mercapto compound or salt thereof of the formula

ZSY wherein Y is selected from the group consisting of hydrogen, a Group I or an equivalent of Group II metal cation or an ammonium cation having up to about 20 carbon atoms or mixtures of two or more of these, and Z is selected from the group consisting of:
   (1) hydrocarbyl groups of the formula —R" having from 4 to about 40 carbon atoms;
   (2) phosphorus acid groups of the formula

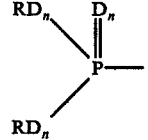

wherein each R is defined as in (A); each $n$ is independently zero or 1; and each D is independently oxygen or divalent sulfur;
   (3) amido-carbo groups of the formula

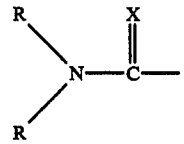

wherein each R and X are defined as in (A);
   (4) hydrocarbyloxycarbo groups and sulfur-containing analogs of the formula

wherein R and D are defined as (B) (2) above; and (5) mixtures of any two or more of any of the groups within (B) (1), (B) (2), (B) (3), and/or (B) (4);

provided that when neither of Q and Q' is hydrocarbyloxy, then Y is a Group I or an equivalent of a Group II metal cation.

2. The composition of claim 1, wherein at least one of Q or Q' is hydrocarbyloxy.

3. The composition of claim 2, wherein X' is oxygen.

4. The composition of claim 3, wherein R is lower alkyl in (A).

5. The composition of claim 4, wherein R' is hydrogen.

6. The composition of claim 5, wherein Z is selected from the group consisting of (B) (1), (B) (2) and mixtures thereof.

7. The composition of claim 6, wherein Y is hydrogen.

8. The composition of claim 7, wherein —R" in (B) (1) is hydrocarbyl of about 8 to about 20 carbon atoms.

9. The composition of claim 8, wherein —R" in (B) (1) is alkyl.

10. The composition of claim 9, wherein X is oxygen.

11. The composition of claim 7, wherein R in (B) (2) is hydrocarbyl of 1 to about 20 carbon atoms.

12. The composition of claim 7, wherein D in (B) (2) is sulfur.

13. The composition of claim 7, wherein D in (B) (2) is oxygen.

14. The composition of claim 7, wherein $n$ is zero in (B) (2).

15. The composition of claim 1, wherein Z is selected from the group consisting of (B) (3), (B) (4) and mixtures thereof; neither of Q and Q' is hydrocarbyloxy; and Y is a Group I or an equivalent of a Group II metal cation.

16. The composition of claim 15, wherein X is oxygen.

17. The composition according to claim 2, wherein X' is a =NH or a =NR$_1$ group wherein R$_1$ is lower alkyl.

18. The composition of claim 17, wherein R is lower alkyl in (A).

19. The composition of claim 18, wherein R' is hydrogen.

20. The composition of claim 19, wherein Z is selected from the group consisting of (B) (1), (B) (2) and mixtures thereof.

21. The composition of claim 20, wherein Y is hydrogen.

22. The composition of claim 21, wherein —R" in B(1) is hydrocarbyl of about 8 to about 20 carbon atoms.

23. The composition of claim 22, wherein —R" is alkyl.

24. The composition of claim 22, wherein X is oxygen.

25. The composition of claim 21, wherein R in (B) (2) is hydrocarbyl of 1 to about 20 carbon atoms.

26. The composition of claim 21, wherein D in B(2) is sulfur.

27. The composition of claim 21, wherein D in B(2) is oxygen.

28. The composition of claim 21, wherein $n$ is zero.

29. The composition of claim 1, wherein Z is (B) (3), (B) (4) or mixtures thereof; Q and Q' are halogen; X and X' are oxygen; R is lower alkyl in (A); R' is hydrogen; and Y is metal.

30. The composition of claim 29, wherein Z is (B) (3) and X is sulfur.

31. A composition according to claim 2, wherein X' is sulfur.

32. The composition of claim 31, wherein R is lower alkyl in (A).

33. The composition of claim 32, wherein R' is hydrogen.

34. The composition of claim 33, wherein Z is selected from the group consisting of (B) (1), (B) (2) and mixtures thereof.

35. The composition of claim 34, wherein Y is hydrogen.

36. The composition of claim 35, wherein —R" in (B) (1) is hydrocarbyl of about 8 to about 20 carbon atoms.

37. The composition of claim 36, wherein —R" in (B) (1) is alkyl.

38. The composition of claim 35, wherein R in (B) (2) is hydrocarbyl of 1 to about 20 carbon atoms.

39. The composition of claim 35, wherein D in (B) (2) is sulfur.

40. The composition of claim 35, wherein D in (B) (2) is oxygen.

41. The composition of claim 35, wherein $n$ is zero in (B) (2).

42. The composition of claim 1, wherein Z is selected from the group consisting of (B) (3), (B) (4) or mixtures thereof; Q and Q' are halogen; X is oxygen; X' is NR$_1$ wherein R$_1$ is lower alkyl; R is lower alkyl in (A); R' is hydrogen; and Y is alkali metal.

43. The composition of claim 2, wherein X' and X are oxygen.

44. The composition of claim 43, wherein R in (A) is lower alkyl and R' is hydrogen.

45. The composition of claim 44, wherein Z is (B) (1), (B) (2) or mixtures thereof.

46. The composition of claim 45, wherein the reaction product of (A) and (B) is further reacted with sulfur.

47. The composition of claim 46, wherein the sulfur is reacted to provide an increase of at least about 0.5% by weight of sulfur based upon the total weight of the product of (A) and (B).

48. The composition of claim 1, wherein at least one of Q and Q' is halogen.

49. The composition of claim 48, wherein the halogen is selected from the group consisting of chloro, bromo, iodo.

50. The composition of claim 49, wherein Y is an alkali metal cation selected from the group consisting of sodium, potassium and mixtures thereof.

51. The composition of claim 50, wherein R in (A) is lower alkyl and R' is hydrogen.

52. The composition of claim 51, wherein Z is (B) (1), (B) (2) or mixtures thereof.

53. The composition of claim 52, wherein Z is (B) (1) and R$^2$ is alkyl of from 8 to about 20 carbon atoms.

54. The composition of claim 52, wherein Z is (B) (1) and R in (B) (2) is hydrocarbyl of from 1 to about 20 carbon atoms.

55. The composition of claim 50, wherein Z is selected from the group consisting of B(3), B(4), and mixtures thereof.

56. The composition of claim 50, wherein Z is a mixture of two or more or B(1), B(2), B(3) and B(4).

57. A fuel or lubricant composition of matter comprising a major amount of a lubricating oil or normally liquid fuel and a minor, oxidation inhibiting amount of a composition of matter which is the reaction mixture made by reacting:

(A) at least one of the substituted di- and triazine compounds of the formula

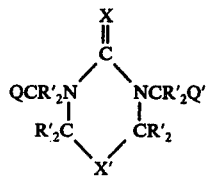

wherein Q and Q' are each independently selected from the group consisting of halo, hydrocarbyloxy of the formula —OR and hydrocarbyl of the formula —R, wherein each R independently contains up to about 20 carbon atoms, with the proviso that at least one of Q and Q' is hydrocarbyloxy or halo; X and X' are each independently selected from the group consisting of oxygen, divalent sulfur, =NH, or =$NR_1$ wherein $R_1$ is as R above; and each R' is independently a hydrogen or a hydrocarbyl of up to about 10 carbon atoms; with (B) at least one mercapto compound or salt thereof of the formula

ZSY wherein Y is selected from the group consisting of hydrogen, a Group I or an equivalent of a Group II metal cation or an ammonium cation having up to about 20 carbon atoms or mixtures of two or more of these and Z is selected from the group consisting of:

(1) hydrocarbyl groups of the formula —R″ having from 4 to about 40 carbon atoms;

(2) phosphorus acid groups of the formula

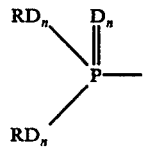

wherein each R is defined as in (A); each n is independently zero or 1; and each D is independently oxygen or divalent sulfur;

(3) amido-carbo groups of the formula

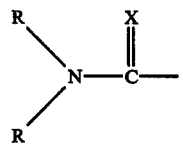

wherein each R and X are defined as in (A);

(4) hydrocarbyloxycarbo groups and sulfur-containing analogs of the formula

wherein R and D are defined as in (B) (2); and (5) mixtures of any two or more of any of the groups within (B) (1), (B) (2), (B) (3), and/or (B) (4);

provided that when neither of Q and Q' is hydrocarbyloxy, then Y is a Group I or an equivalent of a Group II metal cation.

58. A process for making a nitrogen and sulfur-containing composition comprising the step of reacting (A) at least one of the substituted di-and triazine compounds of the formula

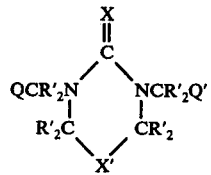

wherein Q and Q' are each independently selected from the group consisting of halo, hydrocarbyloxy of the formula —OR and hydrocarbyl of the formula —R, wherein each R independently contains up to about 20 carbon atoms, with the proviso that at least one Q and Q' is hydrocarbyl or halo; X and X' are each independently selected from the group consisting of oxygen, divalent sulfur, =NH, or =$NR_1$ wherein $R_1$ is as R above; and each $R^1$ is independently a hydrogen or a hydrocarbyl of up to about 10 carbon atoms; with (B) at least one mercapto compound or salt thereof of the formula

ZSY wherein Y is selected from the group consisting of hydrogen, a Group I or an equivalent of a Group II metal cation, or an ammonium cation up to about 20 carbon atoms or mixtures of two or more of these and Z is selected from the group consisting of:

(1) hydrocarbyl groups of the formula —R″ having from 4 to about 40 carbon atoms;

(2) phosphorus acid groups of the formula

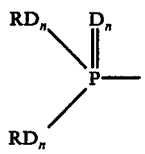

wherein each R is defined as in (A); each n is independently zero or 1; and each D is independently oxygen or divalent sulfur;

(3) amido-carbo groups of the formula

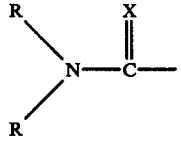

wherein each R and X are defined as above in (A);

(4) hydrocarbyloxycarbo groups and sulfur-containing analogs of the formula

wherein R and D are defined as in (B) (2) above; and (5) mixtures of any two or more of any of the groups within (B) (1), (B) (2), (B) (3), and (B) (4);

provided that when neither of Q and Q' is hydrocarbyloxy, then Y is a Group I or an equivalent of a Group II metal cation.

* * * * *